United States Patent [19]

Vranckx et al.

[11] Patent Number: 5,500,224
[45] Date of Patent: Mar. 19, 1996

[54] PHARMACEUTICAL COMPOSITIONS CONTAINING NANOCAPSULES

[75] Inventors: Henri Vranckx; Martine Demoustier, both of Brussels; Michel Deleers, Linkebeek, all of Belgium

[73] Assignee: U C B S.A., Brussels, Belgium

[21] Appl. No.: 179,205

[22] Filed: Jan. 10, 1994

[30] Foreign Application Priority Data

Jan. 18, 1993 [GB] United Kingdom ............... 9300875

[51] Int. Cl.$^6$ ........................................ A61K 9/51
[52] U.S. Cl. ............... 424/451; 264/4.1; 428/402.2; 428/402.21; 424/455; 424/489; 514/806; 514/808; 514/939; 514/943; 514/951
[58] Field of Search ................ 428/402.22, 402.21, 428/402.2; 264/4.1, 4.3, 4.33, 4.7; 424/489, 451, 455

[56] References Cited

FOREIGN PATENT DOCUMENTS

| | | |
|---|---|---|
| 0447318 | 9/1991 | European Pat. Off. |
| 2515960 | 5/1983 | France. |
| 3341001 | 5/1985 | Germany. |
| 60-061521A | 4/1985 | Japan. |

OTHER PUBLICATIONS

Michel et al., Proceed. Intern. Symp. Control. Rel. Bioact. Mater. 18th, 970–8 Edited by: Kellaway, Ian W., Controlled Release Soc.: Deerfield, Ill. Jan. 1991.

Primary Examiner—Thurman K. Page
Assistant Examiner—James M. Spear
Attorney, Agent, or Firm—Wenderoth, Lind & Ponack

[57] ABSTRACT

A pharmaceutical composition in the form of a colloidal suspension of nanocapsules, comprising an oily phase consisting essentially of an oil containing dissolved therein a surfactant and suspended therein a plurality of nanocapsules having a diameter of less than 500 nanometers, said nanocapsules encapsulating an aqueous phase consisting essentially of a solution or a suspension of a therapeutically active substance, a surfactant and optionally ethanol; a process for preparing the said composition is also described. The walls of said nanocapsules are formed from a poly(alkyl 2-cyanoacrylate) wherein the alkyl radical has 1 to 6 carbon atoms. This composition is particularly suitable for oral administration of polypeptides and polysaccharides.

19 Claims, No Drawings

PHARMACEUTICAL COMPOSITIONS CONTAINING NANOCAPSULES

The present invention relates to new pharmaceutical compositions, and more particularly to pharmaceutical compositions for oral administration, in the form of a colloidal suspension of poly(alkyl-2-cyanoacrylate) nanocapsules in an oily phase, which nanocapsules encapsulate an aqueous solution or suspension of a therapeutically active substance. The invention also relates to a process for preparing such compositions.

Pharmaceutical compositions, in the form of capsules that encapsulate an aqueous phase containing a drug, are already known.

For example, German patent application No. 3341001, discloses nanoparticles and nanocapsules with an average diameter of between 200 and 900 nanometers that encapsulate an aqueous or hydrophilic internal phase containing at least 3% of a medicament or other biologically active substance. The walls of the nanocapsules are formed from the polymerization of a biodegradable monomer, such as an alkyl 2-cyanoacrylate. In order to prepare the nanocapsules, a solution of the monomer in anhydrous chloroform is added to a previously prepared emulsion consisting of an internal hydrophilic phase, for example water or alkalinized methanol containing a solution of the medicament, and an external hydrophobic phase, consisting of a water immiscible organic solvent, for example chloroform, toluene or isooctane, and containing a surface-active agent. In Example 1 of this German patent application No. 3341001, the internal phase is an aqueous solution of methylene blue, the external organic phase is a mixture of chloroform and toluene and the biodegradable monomer is methyl 2-cyanoacrylate. After polymerization, the nanocapsules are separated from the external phase; to this end, the obtained nanocapsules are centrifuged off, then washed copiously and lyophilized, in order to free them of all undesirable organic solvents. The powder so obtained must finally be reformulated in order to give a composition suitable for administration in view of a therapeutic use.

Japanese patent application No. 61521/85 discloses microcapsules with particle diameters of between 1 and 500 micrometers, encapsulating an aqueous phase containing a drug dissolved or suspended in an aqueous solution of a biocompatible polymer such as albumin, dextran, gelatin or collagen. These microcapsules are prepared by adding under stirring an alkyl 2-cyanoacrylate wherein the alkyl radical has 1 to 8 carbon atoms, which is not dissolved in a solvent, to a water-in-oil type emulsion, prepared by adding the aqueous phase to a sparingly water-soluble organic solvent, which, optionally, can contain a surfactant. After the alkyl 2-cyanoacrylate has polymerized at the interface between the two phases, the microcapsules are isolated. To this end, the suspension of microcapsules in the organic solvent is diluted, by the addition of low-boiling hydrocarbon solvents, such as petroleum ether or n-hexane, and then filtered on a membrane filter. The filter residue is copiously washed with the same solvents and then dried under reduced pressure at 40° C., to remove any traces of organic solvents and water. The pharmaceutical preparation so obtained is in the form of microcapsules encapsulating the drug dissolved or suspended in the aqueous solution of the biocompatible polymer. This preparation is intended for administration by injection and, thus, must be reformulated in view of the therapeutic use. More particularly, in the examples given in this Japanese patent application, the organic solvent is cottonseed oil, the biocompatible polymer is bovine serum albumin and the drug is a carcinostatic agent. This Japanese patent application discloses only injectable solutions and no mention of pharmaceutical compositions, suitable for oral administration, is made.

The pharmaceutical compositions prepared according to the aforementioned processes have several important disadvantages.

Firstly, it is well known that, in order to obtain satisfactory absorption of therapeutically active substances through the gastrointestinal tract, it is desirable that the capsules encapsulating such substances are as small as possible. This is the reason why particles having a diameter of less than 1 micrometer are most suitable to prepare a pharmaceutical composition intended for oral administration. However, the microcapsules prepared according to the process described in Japanese patent application No. 61521/85, always have a particle diameter greater than 1 micrometer and, generally, a diameter of between 1 and 500 micrometers.

Secondly, the organic solvents (isooctane, alkalinized methanol, chloroform, toluene and petroleum ether), which are typically necessary to prepare the capsules, are pharmaceutically unacceptable on account of their high toxicity. Thus, the so prepared capsules cannot be administered directly after preparation. This gives rise consequently to the implementation of a delicate supplementary step which includes the separation of the capsules, for example by filtration on a membrane filter or by ultracentrifugation, followed by a thorough purification, in order to remove any traces of any therapeutically incompatible solvents. After purification, the capsules then must be reformulated adequately to be administrable without difficulty.

Thirdly, in certain cases, such as in the aforementioned Japanese patent application, the preparation of the capsules requires mandatorily the presence of a macromolecule, for example bovine serum albumin or dextran. However, it is to be noted that such macromolecules, which have an animal origin, can cause undesirable immunological reactions and that the anaphylactic shocks, which can be caused by dextrans, are spectacular and well known.

Since oral administration remains a preferred route for administering medicaments, injections being considered in general as more painful and disliked by patients and since submicroscopic capsules encapsulating active pharmaceutical substances have produced encouraging results, when used as carriers for medicaments, particularly for administration by a parenteral route, it would be of great interest to provide pharmaceutical compositions, for oral administration, in the form of submicroscopic capsules encapsulating a solution or suspension of a therapeutically active substance in an aqueous phase, but which do not suffer the aforementioned disadvantages of the known pharmaceutical compositions.

Indeed, this type of administration in the form of submicroscopic capsules is necessary, principally in the case of medicaments which can be degraded in the stomach, such as drugs with a peptide structure.

Particularly, the submicroscopic capsules should be formed from a biodegradable material, they should be sufficiently small for there has to be a good prospect of satisfactory absorption in the gastro-intestinal tract and, at the same time, the capsules should encapsulate an important amount of pharmaceutically active substance. In addition, if such compositions were suitable for administration directly after production, without the need for subsequent isolation, purification and reformulation steps, this would constitute an important technical simplification and a not insignificant advantage.

We have now discovered new pharmaceutical compositions in the form of nanocapsules which fully attain all these objects. Thus, according to the present invention, there is provided a pharmaceutical composition in the form of a colloidal suspension of nanocapsules, comprising an oily phase consisting essentially of an oil containing a surfactant and, suspended therein, a plurality of nanocapsules having a diameter of less than 500 nanometers, said nanocapsules encapsulating an aqueous phase consisting essentially of a solution or a suspension of a therapeutically active substance and a surfactant in water, whose pH lies between 1 and 7, whereby the walls of said nanocapsules are formed from a poly(alkyl 2-cyanoacrylate) wherein the alkyl radical has 1 to 6 carbon atoms.

According to another aspect, the present invention provides a process for preparing a pharmaceutical composition, comprising:

a) preparing an aqueous phase consisting essentially of a solution or a suspension of a therapeutically active substance and a surfactant in water, whose pH lies between 1 and 7;

b) adding slowly and under stirring said aqueous phase into an oily phase consisting essentially of an oil and a surfactant dissolved therein, in order to form a water-in-oil type emulsion;

c) adding under stirring to said water-in-oil type emulsion at least one alkyl 2-cyanoacrylate wherein the alkyl radical has 1 to 6 carbon atoms, just as it is, in the absence of a solvent, allowing the alkyl 2-cyanoacrylate to polymerize at ambient temperature for a sufficient period of time to polymerize the added alkyl 2-cyanoacrylate and recovering as product of the process a suspension in the oily phase of nanocapsules having a diameter of less than 500 nanometers and which encapsulate the said aqueous phase.

The oily phase of the pharmaceutical compositions according to the invention consists essentially of a neutral pharmaceutically acceptable oil containing a dissolved surfactant. Said oil can be a vegetable oil, a mineral oil or any oily compound, insoluble in water, such as benzyl benzoate or glycerides of higher $C_6$ to $C_{18}$ fatty acids. Among the latter, use is preferably made of MIGLYOL, for example a MIGLYOL 812, which is a neutral oil formed from a mixture of saturated fatty acids triglycerides, with chain lengths essentially of about 8 to 10 carbon atoms.

The aqueous phase, contained in the central cavity of the nanocapsules of the pharmaceutical compositions according to the invention, consists essentially of a solution or suspension of a water-soluble or insoluble therapeutically active substance, and contains also a surfactant. This aqueous phase contains preferably also a certain amount of ethanol, which has the effect of making the walls of the nanocapsules more rigid. The amount of ethanol, which may be added to the aqueous phase, is preferably between 100 μl and 1000 μl per ml of the aqueous phase and, more preferably, between 200 μl and 500 μl per ml of the aqueous phase.

According to the invention, the pH of the aqueous phase should be adjusted to between 1 and 7 by means of a pharmaceutically acceptable acid or suitable buffer, for example by means of an acetic buffer to provide a pH of 4.3. If the pH exceeds a value of 7, the diameter of the capsules obtained exceeds 500 nanometers and may even become greater than one micrometer.

The ratio by volume of the aqueous phase to the oily phase preferably lies between 1:100 and 20:100 and, more preferably, is between 5:100 and 15:100.

The surfactants which can be used in the pharmaceutical compositions, according to the invention are pharmaceutically acceptable surfactants. They include natural surfactants, such as deoxycholic acid or other bile acid salts or their derivatives, and synthetic surfactants. In the latter case, an anionic type (such as sodium laurylsulfate or sodium dioctylsulfosuccinate), a cationic type (such as quaternary ammonium salts), or a non-ionic type (such as fatty acid esters of sorbitan or of polyoxyethylene sorbitan, for example Span 80, or mixed derivatives of ethylene oxide and propylene glycol, for example, Pluronic F68) can be employed.

We have found by suitable tests that surfactants must be present simultaneously in the aqueous phase and in the oily phase, in order to ensure that the nanocapsules according to the invention have a diameter of less than 500 nanometers and, preferably, one greater than 80 nanometers.

The surfactants, respectively, are dissolved in the appropriate liquid constituting the internal aqueous phase or the external oily phase. In the aqueous phase for example, suitable surfactants include sodium laurylsulfate, sodium dioctylsulfosuccinate, polyoxyethylene sorbitan fatty acid esters, mixed derivatives of ethylene oxide and propylene glycol or polyoxyethylene glycol and, preferably, sodium laurylsulfate. In the oily phase, the surfactants include sorbitan fatty acid esters or soluble salts of bile acids and, preferably, sorbitan mono-oleate (Span 80) or deoxycholic acid.

The concentration of the surfactant in the aqueous phase generally lies between 0.1% and 10%, preferably between 3% and 5%, by weight of surfactant per volume of aqueous phase.

The concentration of surfactant in the oily phase, generally, lies between 0.1% and 20%, preferably, between 5% and 15% by weight of surfactant per volume of oily phase.

The walls of the nanocapsules in suspension in the pharmaceutical compositions according to the invention are formed from a biodegradable poly(alkyl 2-cyanoacrylate), obtained by micellar polymerization of at least one alkyl 2-cyanoacrylate wherein the alkyl radical, which may be a linear or branched chain radical, has 1 to 6 carbon atoms. The most suitable poly(alkyl 2-cyanoacrylates) for the present invention are obtained by micellar polymerization of n-butyl 2-cyanoacrylate and n-hexyl 2-cyanoacrylate. These alkyl 2-cyanoacrylates may be used alone or in admixture, given that the walls of the nanocapsules can consist of polymers or copolymers of alkyl 2-cyanoacrylates.

The alkyl 2-cyanoacrylate is added to the polymerization medium just as it is, without any solvent. According to the invention, this polymerization can be carried out at ambient temperature for a period, preferably, of between 3 and 8 hours.

The therapeutically active substance, used in the pharmaceutical compositions according to the invention, is contained in the aqueous phase present in the central cavity of the nanocapsules. Any drug, including those which are soluble in water and those that are sparingly soluble in water, can be used in these compositions. The new compositions according to the invention are particularly suitable for encapsulating polypeptides, such as calcitonin, somatostatin or insulin and polysaccharides such as heparin. It is well known that these compounds are very rapidly degraded by the proteolytic enzymes present in the gastrointestinal tract, after oral administration.

On the contrary, the compositions according to the invention containing the same compounds show significant pharmaceutical activity when they are administered by this same route, thanks to encapsulation of the active principle.

The pharmaceutical compositions according to the invention and the process for preparing the same as described hereinabove, provide considerable advantages over the prior art, including the following:

- the nanocapsules obtained have a diameter of less than 500 nanometers and, preferably, one of 80 to 450 nanometers, resulting in excellent absorption through the intestinal mucous membrane;
- the nanocapsules have excellent physical stability over a period of at least 18 months at both ambient temperature and 4° C.;
- in view of the complete absence of organic solvents during the preparation of the nanocapsules and of the pharmaceutical composition, laborious separation and purification of the nanocapsules in order to remove any traces of any therapeutically incompatible solvent is no longer necessary;
- in view of the absence of macromolecules of animal origin, such as albumin or dextran, there is no risk of undesirable immunological reactions (such as anaphylactic shock)
- since all the constituents (oil, water, surfactants) have been chosen from pharmaceutically acceptable substances, the process of the invention results in the formation of a ready-to-use pharmaceutical composition whose innocuous nature is ensured. Thus, the resulting composition can be administered directly by oral route, (or possibly also intramuscularly) without any need for prior isolation, purification and redispersion in a suitable medium of the nanocapsules. Further, the composition of the invention can be used directly in gelatine capsules for oral administration;
- the pharmaceutical composition is prepared by a process which is simple and can easily be transposed to an industrial scale.

The examples which follows are given in order to illustrate the invention without limiting it. Examples 1 to 5 and 8 relate particularly to the process for preparing a suspension in oil of nanocapsules encapsulating an aqueous phase and examples 6, 7 and 9 to 16 illustrate a pharmaceutical composition in the form of nanocapsules encapsulating a therapeutically active substance.

The physical stability of the pharmaceutical preparation so obtained is determined by direct observation of the absence of appearance of two distinct phases, aqueous and oily, after several months storage, as well as by measurement, at regular intervals, of the average size of the nanocapsules dispersed in the oil. The average size of the nanocapsules is measured by means of a Coulter Model N4MD Sub-micron Particle Analyser.

EXAMPLE 1

1 ml of aqueous acetic buffer at pH 4.3* containing 5 % by weight per volume of sodium laurylsulfate, is added slowly at ambient temperature, with vigorous stirring (1200 rpm) to 10 ml MIGLYOL 812 (neutral oil consisting of a mixture of $C_8$ to C10 saturated fatty acid triglycerides) containing 15% by weight per volume of sorbitan monooleate (Span 80). The suspension is stirred under the same conditions for 15 minutes, then 100 μl of n-butyl 2-cyanoacrylate are added and polymerization of the monomer allowed to take place for 240 minutes. A suspension in oil of nanocapsules which encapsulate an aqueous phase and have an average diameter of 255 nanometers is thereby obtained.
*Buffer composition: glacial acetic acid 2 g, sodium acetate 2 g, sodium chloride 7.5 g, demineralized water to 1 liter.

These nanocapsules do not exhibit any significant variation in size after storage for at least 18 months at ordinary temperature and at 4° C.

EXAMPLE 2

Nanocapsules are prepared using the process described in example 1, but the aqueous acetic buffer is replaced by an aqueous phosphate buffer at pH 7 (buffer composition: 39 ml of a 0.2 molar solution of $NaH_2PO_4.H_2O$, 61 ml of a 0.2 molar solution of $Na_2HPO_4.2H_2O$ and 100 ml of distilled water).

The resulting nanocapsules which encapsulate an aqueous phase, have an average size of 422 nanometers.

EXAMPLE 3

The same conditions are used as in example 1, but in addition, the aqueous phase contains 0.25 mg of a water-insoluble coloring agent in suspension (FDC Blue 2 HT Aluminium Lake, cert. n° AA2041, Colorcon).

The nanocapsules so obtained encapsulate an aqueous suspension of the coloring agent and have an average size of 246 nanometers.

EXAMPLE 4

Nanocapsules are prepared using the same process as in example 1, but this time, the oily phase is MIGLYOL 829 (oil consisting of a mixture of $C_8$ to $C_{10}$ saturated fatty acid triglycerides and 15 to 20% of succinic acid).

The resulting nanocapsules which encapsulate an aqueous phase, have an average size of 246 nanometers.

EXAMPLE 5

Nanocapsules are prepared according to the process of example 1, but the n-butyl 2-cyanoacrylate is replaced by n-hexyl 2-cyanoacrylate and polymerization is allowed to take place for 8 hours.

The resulting nanocapsules which encapsulate an aqueous phase, have an average size of 213 nanometers. The physical stability of these nanocapsules is excellent; no significant variation in their size is observed after storage for at least 12 months at ordinary temperature.

EXAMPLE 6

The procedure of example 1 is followed, but the aqueous phase also contains 1100 IU of calcitonin.

The nanocapsules so obtained have an average size of 177 nanometers and the aqueous phase contained therein includes the calcitonin.

The physical stability of these nanocapsules is excellent; there is no significant variation in their size after at least 12 months storage at ambient temperature or at 4° C.

EXAMPLE 7

Nanocapsules are prepared according to the process of example 1, but the n-butyl 2-cyanoacrylate is replaced by n-hexyl 2-cyanoacrylate and the aqueous phase contains in addition 1100 IU of calcitonin. After 4 hours of polymerization, nanocapsules in which the aqueous phase contained therein includes the medicament, and having an average size of 211 nanometers, are obtained. The physical stability of these capsules is excellent, there is no significant variation in their size when stored for at least 11 months at ordinary temperature and at 4° C.

EXAMPLE 8

The procedure of example 1 is followed, but the aqueous phase contains 400 μl of ethanol.

After 4 hours of polymerization, nanocapsules which encapsulate an aqueous phase and have an average size of 211 nanometers are obtained. The physical stability of these nanocapsules is excellent; no significant variation in their size is apparent after at least 12 months storage at ambient temperature or at 4° C.

These nanocapsules which encapsulate a small amount of ethanol, have a greater wall rigidity than the nanocapsules prepared in example 1, which do not contain ethanol.

This wall rigidity is determined by a centrifuging test, in which a suspension in oil of the nanocapsules is subjected to a centrifugation at 20,000 revolutions per minute for 2 hours. The nanocapsules prepared in this example are able to stand up to this test without damage.

EXAMPLE 9

Using the process of example 8, nanocapsules are prepared in which the aqueous phase is a solution of 0.025 % (weight per volume) of methylene blue in water. The nanocapsules so obtained have an average size of 205 nanometers. The percentage of coloring agent encapsulated reaches 98.3%.

EXAMPLE 10

Using the process of example 8, nanocapsules are prepared in which the aqueous phase contains 300 USP units of heparin. The nanocapsules so obtained have an average size of 137 nanometers.

EXAMPLE 11

Using the process of example 8, nanocapsules are prepared in which the aqueous phase contains 0.9 mg of somatostatin. The nanocapsules so obtained have an average size of 201 nanometers.

EXAMPLE 12

Using the process of example 8, nanocapsules are prepared in which the aqueous phase contains 11,000 IU of calcitonin. The average size of the nanocapsules in suspension in this preparation is 211 nanometers. Deoxycholic acid dispersed in Miglyol 812 is added in order to obtain a 0.02 molar concentration of deoxycholic acid in the mixture.

EXAMPLE 13

The process of in example 12 is followed, but the aqueous phase contains 110,000 IU of calcitonin. The average size of the nanocapsules so obtained is 225 nanometers.

EXAMPLE 14

The purpose of this example is to compare the effectiveness of different calcitonin preparations administered to rats by different routes: oral, duodenal, ileal and intravenous.

The physiological response, to the administration of calcitonin in an organism, is revealed by a reduction in the level of calcium circulating freely in the blood.

The suspension of nanocapsules encapsulating calcitonin from example 13 is given to male Wistar rats (weight: 200±20 g), anaesthetized with pentobarbital (60 mg/kg), at a dose of 20 IU of calcitonin per animal, by oral, duodenal or ileal administration.

For comparison, the same dose of calcitonin is administered intravenously in aqueous solution to control rats.

Blood samples are taken at regular intervals from a caudal vein. After coagulating and centrifuging the blood, (2×10 minutes at 6,000 rpm), the sera are diluted and assayed for calcium using an atomic absorption spectrometer.

The assay results for each mode of administration are then plotted on a graph representing the percentage of calcium in the serum as a function of time. The areas under the resulting curves corresponding to administration by the oral, duodenal or ileal routes are calculated and compared with the area under that derived from the results for intravenous administration, which gives the maximum activity observed and which is arbitrarily defined as 100% activity.

The results of these tests show that 4 hours after the calcitonin preparation has been administered to the animal, either orally or directly into the duodenum or ileum, there is found, in all cases, a reduction in the serum calcium level corresponding to 73% of the effect produced by intravenous administration of the same dose of calcitonin. The activity obtained by oral administration of a pharmaceutical composition according to the invention, therefore, is as good as that observed after administration of the same preparation by the more delicate intraduodenal or ileal routes.

EXAMPLE 15

The process of example 1 is followed, but the aqueous acetic buffer at pH 4.3 is replaced by an aqueous acetic buffer at pH 3.6*. Further, the aqueous phase also contains 780 IU of bovine zinc-insulin and 200 μl of ethanol.

*Buffer composition: 46.3 ml of a 0.2 molar solution of glacial acetic acid, 3.7 ml of a 0.2 molar solution acetate and 50 ml of distilled water.

The nanocapsules so obtained encapsulate an aqueous phase and have an average size of 260 nanometers.

EXAMPLE 16

Influence of Ethanol on Nanocapsule Rigidity

The observations of example 8 as to rigidity of the walls of the nanocapsules in the presence or in the absence of ethanol in the aqueous phase are confirmed by the test carried out in this example.

Using the test conditions described in example 14, the composition prepared in example 12, which contains 400 μl of ethanol and 0.02 mole of deoxycholic acid, and a composition prepared according to the same process as described in example 12 but without any ethanol, are administered orally to rats. The results obtained are compared, as in example 14, with the effect obtained by intravenous injection of an identical dose of calcitonin in aqueous solution.

The results obtained are set out in Table I. Column 3 of this Table gives the reduction in percent of the serum calcium levels after four hours.

TABLE I

| Administration route | Amount of ethanol (μl) | Calcium level (reduction in %) |
|---|---|---|
| Oral | — | 7 |
| Oral | 400 | 48 |
| Intravenous | — | 100 |

This Table shows that the composition, which does not contain ethanol, only causes a reduction in the serum calcium level of 7%, after four hours, whereas the composition containing alcohol produced a reduction of 48%.

This difference may be explained by the fact that the ethanol free nanocapsules have less rigid walls. Therefore, a large number of these nanocapsules are ruptured, during their passage through the stomach, where a significant amount of calcitonin is released and digested by the action of proteolytic enzymes. Thus, a smaller quantity of calcitonin only reaches the intestine, where it is effectively resorbed, inducing therefore a physiological response of less intensity.

EXAMPLE 17 (comparative)

Using the process of example 8, an attempt is made to prepare nanocapsules in which the aqueous phase contains an increasing amount of bovine serum albumin (BSA n° A-8022, marketed by Sigma Corp.) equal to 50, 100, 150 and 300 mg per milliliter of the aqueous phase.

Using the process of example 12, an attempt is also made to prepare nanocapsules in which the aqueous phase contains 300 mg/ml of BSA.

In all cases the resulting preparation contains two populations of capsules, which have different average sizes.

Table II gives the average sizes of these capsules and the percentage of each of the two capsule populations obtained as a function of the bovin serum albumin content in the aqueous phase.

TABLE II

| BSA (mg/ml) | Calcitonin (IU) | Average size of capsules (nm) | Percentage |
|---|---|---|---|
| 50 | — | 294 | 75 |
|  |  | 3000 | 25 |
| 100 | — | 215 | 30 |
|  |  | 1040 | 70 |
| 150 | — | 520 | 22 |
|  |  | 1930 | 78 |
| 300 | — | 225 | 2 |
|  |  | 2610 | 98 |
| 300 | 1100 | 225 | 1 |
|  |  | 4690 | 99 |

The results of Table II show that if a biopolymer, such as bovine serum albumin (BSA), is present in the aqueous phase (as described in Japanese patent application 61521/85), the resulting composition is not according to the invention because it does not contain a homogeneous population of nanocapsules having an average size of less than 500 nanometers. The percentage of nanocapsules decreases as the amount of BSA present in the aqueous phase increases and is practically nil when this amount is equal to 300 mg of BSA per milliliter of aqueous phase.

We claim:

1. A pharmaceutical composition in the form of a colloidal suspension of nanocapsules, comprising an oily phase consisting essentially of an oil, wherein the oil is a vegetable oil, a mineral oil or an oily compound selected from benzyl benzoate and glycerides of higher fatty acids, said oil containing dissolved therein a surfactant and, suspended therein, a plurality of nanocapsules having a diameter of less than 500 nanometers, said nanocapsules encapsulating an aqueous phase consisting essentially of a solution or a suspension of a therapeutically active substance and a surfactant in water, whose pH lies between 1 and 7, whereby the walls of said nanocapsules are formed from a poly(alkyl 2-cyanoacrylate) wherein the alkyl radical has 1 to 6 carbon atoms, all constituents of said composition being chosen from pharmaceutically acceptable substances.

2. A pharmaceutical composition as claimed in claim 1, wherein the therapeutically active substance is a polypeptide or a polysaccharide.

3. A pharmaceutical composition as claimed in claim 1, wherein the therapeutically active substance is calcitonin, somatostatin, insulin or heparin.

4. A pharmaceutical composition as claimed in claim 1, wherein the aqueous phase further contains between 100 µl and 1,000 µl, of ethanol per milliliter thereof.

5. A pharmaceutical composition as claimed in claim 4, wherein the aqueous phase contains between 200 µl and 500 µl of ethanol per milliliter thereof.

6. A process for preparing a pharmaceutical composition as claimed in claim 1, comprising:

a) preparing an aqueous phase consisting essentially of a solution or a suspension of a therapeutically active substance and a surfactant in water, whose pH lies between 1 and 7;

b) adding slowly and under stirring said aqueous phase into an oily phase consisting essentially of an oil wherein the oil is a vegetable oil, a mineral oil or an oily compound selected from benzyl benzoate and glycerides of higher fatty acids, said oil containing a surfactant dissolved therein, in order to form a water-in-oil emulsion;

c) adding under stirring to said water-in-oil emulsion, at least one alkyl 2-cyanoacrylate wherein the alkyl radical has 1 to 6 carbon atoms, just as it is, in the absence of a solvent, allowing the alkyl 2-cyanoacrylate to polymerize at ambient temperature for a sufficient period of time to polymerize the added alkyl 2-cyanoacrylate, and recovering as product of the process a suspension in the oily phase of nanocapsules having a diameter of less than 500 nanometers and which encapsulate the said aqueous phase, all constituents of said composition being chosen from pharmaceutically acceptable substances.

7. A pharmaceutical composition as claimed in claim 1, wherein the ratio by volume of the aqueous phase to the oily phase is from 1:100 to 20:100.

8. A pharmaceutical composition as claimed in claim 7, wherein the ratio by volume of the aqueous phase to the oily phase is from 5:100 to 15:100.

9. A pharmaceutical composition as claimed in claim 1, wherein the surfactant in the aqueous phase is selected from the group consisting of sodium laurylsulfate, sodium dioctylsulfosuccinate, polyoxyethylene sorbitan fatty acid esters, mixed products of ethylene oxide (s) and propylene glycol (s) and polyoxyethylene glycol.

10. A pharmaceutical composition as claimed in claim 1 wherein the concentration of surfactant in the aqueous phase is between 0.1% and 10%, by weight of surfactant per volume of aqueous phase.

11. A pharmaceutical composition as claimed in claim 1, wherein the surfactant in the oily phase is selected from the group consisting of sorbitan fatty acid esters and soluble salts of bile acids.

12. A pharmaceutical composition as claimed in claim 1, wherein the concentration of surfactant in the oily phase is between 0.1% and 20% by weight of the surfactant per volume of oily phase.

13. A process claimed in claim 6, wherein the concentration of surfactant in the oily phase is between 0.1% and 20% by weight of the surfactant per volume of oily phase.

14. A process as claimed in claim 6, wherein the polymerization of the alkyl 2-cyanoacrylate is carried out for a period of between 3 and 8 hours.

15. A process as claimed in claim 6, wherein the therapeutically active substance is calcitonin, somatostatin, insulin or heparin.

16. A process as claimed in claim 6, wherein the aqueous phase further contains between 100 μl and 1,000 μl of ethanol per milliliter thereof.

17. A process as claimed in claim 6, wherein the surfactant in the aqueous phase is sodium laurylsulfate.

18. A process as claimed in claim 6, wherein the concentration of surfactant in the aqueous phase is between 0.1% and 10% by weight of surfactant per volume of aqueous phase.

19. A process as claimed in claim 6, wherein the surfactant in the oily phase is sorbitan mono-oleate.

* * * * *